United States Patent
Chang et al.

(10) Patent No.: US 9,493,347 B2
(45) Date of Patent: Nov. 15, 2016

(54) METHOD OF FORMING A SEMICONDUCTOR DEVICE

(71) Applicant: TAIWAN SEMICONDUCTOR MANUFACTURING COMPANY, LTD., Hsinchu (TW)

(72) Inventors: Yi-Hsien Chang, Shetou Township (TW); Chun-Ren Cheng, Hsinchu (TW); Yi-Shao Liu, Zhubei (TW); Allen Timothy Chang, Hsinchu (TW); Ching-Ray Chen, Taipei (TW); Yeh-Tseng Li, Zhubei (TW); Wen-Hsiang Lin, Jhudong Township (TW)

(73) Assignee: TAIWAN SEMICONDUCTOR MANUFACTURING COMPANY, LTD. (TW)

( * ) Notice: Subject to any disclaimer, the term of this patent is extended or adjusted under 35 U.S.C. 154(b) by 0 days.

(21) Appl. No.: 14/508,194

(22) Filed: Oct. 7, 2014

(65) Prior Publication Data
US 2015/0024533 A1    Jan. 22, 2015

Related U.S. Application Data

(63) Continuation of application No. 13/465,928, filed on May 7, 2012, now Pat. No. 8,883,021.

(60) Provisional application No. 61/617,834, filed on Mar. 30, 2012.

(51) Int. Cl.
*B23P 15/00*    (2006.01)
*C03C 25/00*    (2006.01)
(Continued)

(52) U.S. Cl.
CPC ....... *B81C 1/00349* (2013.01); *B81C 1/00206* (2013.01); *B81C 1/00214* (2013.01);
(Continued)

(58) Field of Classification Search
CPC ................... G01N 27/44791; B81C 1/00349; B81C 1/00206
USPC .......................................................... 216/39
See application file for complete search history.

(56) References Cited

U.S. PATENT DOCUMENTS 5,503,882 A    4/1996    Dawson
5,702,981 A *  12/1997   Maniar et al. ................ 438/627
(Continued)

FOREIGN PATENT DOCUMENTS

CN    102227659    10/2011
TW    201003733    1/2010

OTHER PUBLICATIONS

Office Action dated Oct. 7, 2014 from corresponding No. TW 101128380.
(Continued)

Primary Examiner — Thomas Pham
(74) Attorney, Agent, or Firm — Hauptman Ham, LLP

(57) ABSTRACT

A method of forming a semiconductor device includes depositing a light reflecting layer over a substrate. The method also includes forming a protection layer over the light reflecting layer. The method further includes forming an anti-reflective coating (ARC) layer over the protection layer. The method additionally includes forming an opening in the ARC layer, the protection layer and the light reflecting layer exposing the substrate. The method also includes removing the ARC layer in a wet solution comprising H2O2, the ARC layer being exposed to the $H_2O_2$ at a flow rate greater than about 10 standard cubic centimeters per minute (sccm).

20 Claims, 12 Drawing Sheets

(51) Int. Cl.
*C23F 1/00* (2006.01)
*B44C 1/22* (2006.01)
*C03C 25/68* (2006.01)
*C25F 3/00* (2006.01)
*B81C 1/00* (2006.01)
*G01N 27/447* (2006.01)
*B82Y 20/00* (2011.01)

(52) U.S. Cl.
CPC ...... *B81B2201/042* (2013.01); *B81C 1/00111* (2013.01); *B82Y 20/00* (2013.01); *G01N 27/44791* (2013.01)

(56) References Cited

U.S. PATENT DOCUMENTS

| | | | | |
|---|---|---|---|---|
| 5,719,085 | A * | 2/1998 | Moon et al. | 438/424 |
| 5,882,999 | A * | 3/1999 | Anderson et al. | 438/629 |
| 6,028,014 | A * | 2/2000 | Sukjarev | C23C 16/402 438/5 |
| 6,028,325 | A | 2/2000 | Yamazaki | |
| 2001/0046791 | A1 | 11/2001 | Subramanian et al. | |
| 2003/0160208 | A1 * | 8/2003 | Yeo et al. | 252/79.1 |
| 2006/0272677 | A1 * | 12/2006 | Lee et al. | 134/3 |
| 2007/0218623 | A1 | 9/2007 | Chua et al. | |
| 2008/0261399 | A1 * | 10/2008 | Choi et al. | 438/692 |
| 2009/0258495 | A1 * | 10/2009 | Chan et al. | 438/694 |
| 2010/0099100 | A1 * | 4/2010 | Zaccarin et al. | 435/6 |
| 2011/0222179 | A1 * | 9/2011 | Monadgemi | 359/850 |
| 2011/0257040 | A1 * | 10/2011 | Turner et al. | 506/16 |
| 2012/0091522 | A1 * | 4/2012 | Ozaki et al. | 257/330 |

OTHER PUBLICATIONS

Wang, Zhanguo et al., "Information Functional Materials Manual", Beijing: Chemical Industry Press, Jun. 2009; ISBN 978-7-122-05338-1; http://www.cip.com.cn/; two pages have been retrieved from http://img.duxiu.com/n/print.jsp and http://www.yuyanwz.cn/n/print.jsp. English Abstract is attached.

Office Action dated Mar. 17, 2016 from corresponding No. CN 201210279330.X.

* cited by examiner

METHOD OF FORMING A SEMICONDUCTOR DEVICE

PRIORITY CLAIM

The present application is a continuation of U.S. application Ser. No. 13/465,928, filed May 7, 2012, which claims the priority of U.S. Provisional Application No. 61/617,834, filed Mar. 30, 2012, which are incorporated herein by reference in their entireties.

TECHNICAL FIELD

This disclosure relates to MEMS nanostructures and methods for forming MEMS nanostructures.

BACKGROUND

A fabrication technology of microelectromechanical systems (MEMS) involves forming micro-structures with dimensions in the micrometer scale (one millionth of a meter) in order to implement mechanical, fluidic, optical, biological and/or electrical systems. Significant parts of the fabrication technology have been adopted from integrated circuit (IC) technology, including cleaning, layering, patterning, etching or doping steps.

MEMS applications include inertial sensors applications, such as motion sensors, accelerometers, and gyroscopes. Other MEMS applications include optical applications such as movable mirrors, RF applications such as RF switches and resonators, and biological sensing structures. Despite the attractive applications noted above, a number of challenges exist in connection with developing MEMS nanostructures. Various techniques directed at configurations and methods of forming these MEMS nanostructures have been implemented to try and further improve device performances.

BRIEF DESCRIPTION OF THE DRAWINGS

Aspects of the present disclosure may be understood from the following detailed description and the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiment in which additional features may be formed interposing the first and second features, such that the first and second features may not be in direct contact. Further still, references to relative terms such as "top", "front", "bottom", and "back" are used to provide a relative relationship between elements and are not intended to imply any absolute direction. Various features may be arbitrarily drawn in different scales for simplicity and clarity.

Figure 1:
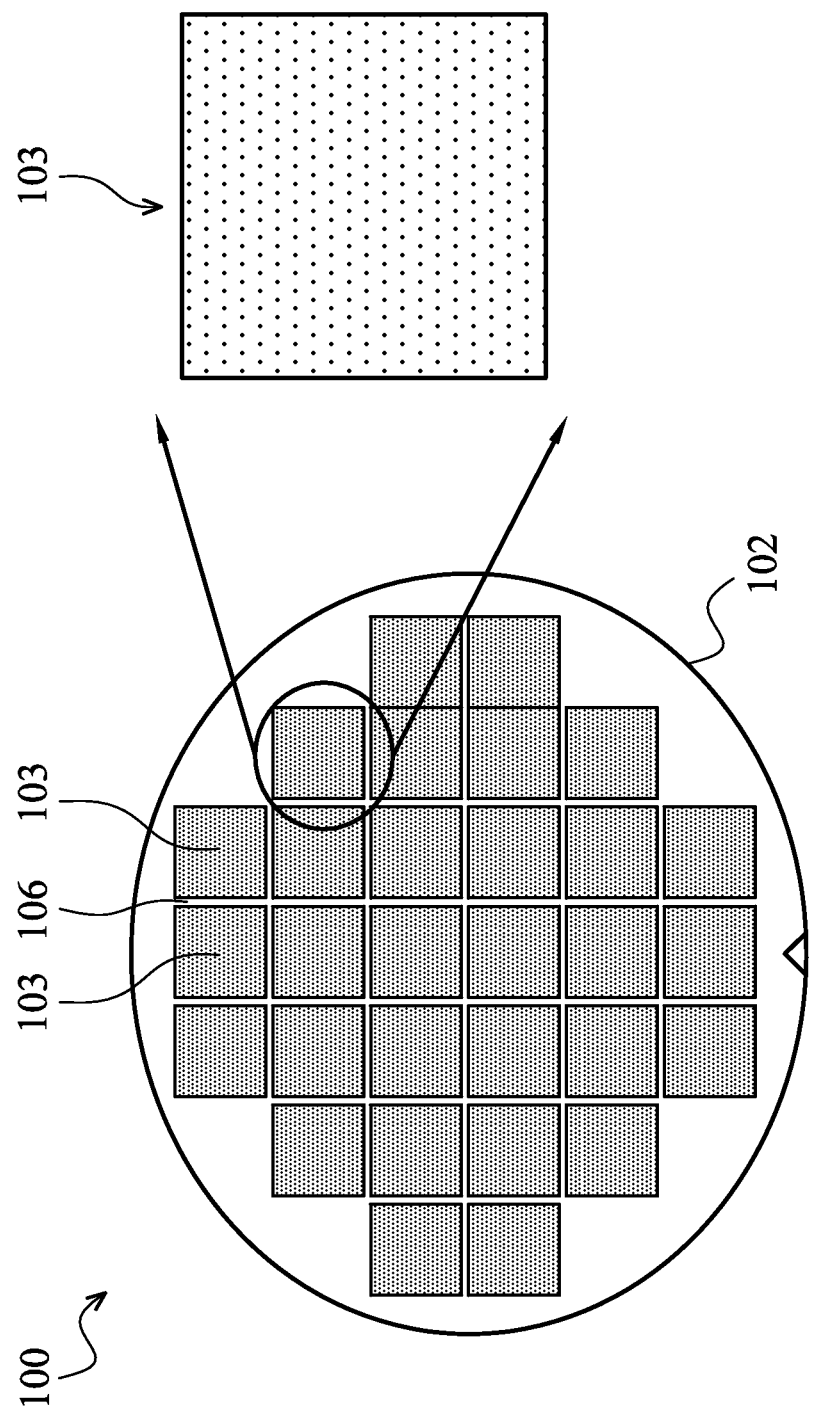
FIG. 1A is a top view of a wafer including a plurality of MEMS chips on a substrate according to one or more embodiments of this disclosure.
FIG. 1B is an enlarged view of a single MEMS chip of FIG. 1A according to one or more embodiments of this disclosure.

FIG. 1A is a top view of a wafer 100 including a plurality of MEMS chips 103 marked on a substrate 102. The plurality of MEMS chips 103 are divided by scribe lines 106 between the MEMS chips 103. FIG. 1B is an enlarged view of a single MEMS chip 103 depicted in FIG. 1A. The substrate 102 will go through a variety of cleaning, layering, patterning, etching or doping steps to form MEMS nanostructures in the MEMS chips 103. The term "substrate" herein generally refers to a bulk substrate that is suitable for transmitting electrical or optical signals of an analyte. In at least one example, the substrate 102 includes a transparent material, such as quartz, sapphire, fused silica or other suitable glasses. In another example, the substrate is a rigid material which keeps the observed analyte in fixed positions during observation. In yet another example, the substrate 102 is a transparent organic material, for example, methacrylate polymers such as PMMA, polycarbonates, cyclic olefin polymers, styrenic polymers, fluorine-containing polymers, polyesters, polyetherketones, polyethersulfones, polyimides or mixtures thereof. In some embodiments, various layers and devices structures are formed over the substrate 102. Examples of such layers include dielectric layers, doped layers, polysilicon layers or conductive layers. Examples of device structures include transistors, resistors, and/or capacitors, which may be interconnected through an interconnect layer to additional devices.

Figure 2:
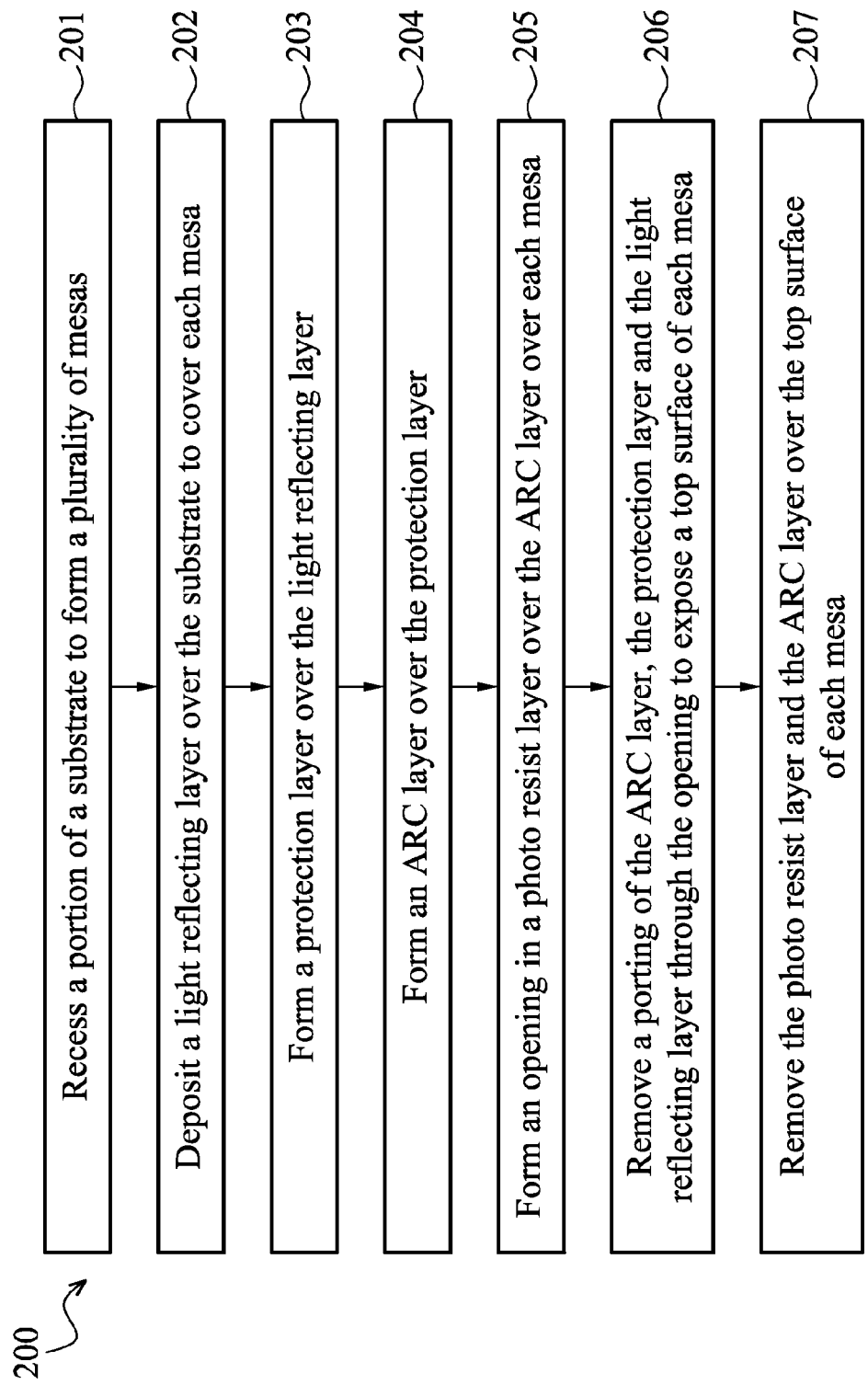
FIG. 2 is a flowchart of a method of forming a structure of a MEMS chip having a MEMS nanostructure according to one or more embodiments of this disclosure.

FIG. 2 is a flowchart of a method 200 of forming a structure in a MEMS chip having a MEMS nanostructure according to one or more embodiments of this disclosure. The method 200 may include forming the MEMS nanostructure using one or more process steps compatible with a complementary metal-oxide-semiconductor (CMOS) process. The flow chart of the method 200 begins with operation 201 in which a portion of a substrate is recessed to form a plurality of mesas. Next, the method 200 continues with operation 202 in which a light reflecting layer is deposited over the substrate to cover each mesa. The method 200 continues with operation 203 in which a protection layer is formed over the light reflecting layer. The method 200 continues with operation 204 in which an anti-reflective coating (ARC) layer is formed over the protection layer. The method 200 continues with operation 205 in which an opening is formed in a photo resist layer over the ARC layer over each mesa. The method 200 continues with operation 206 in which a portion of the ARC layer, the protection layer and the light reflecting layer are removed through the opening to expose a top surface of each mesa. The method 200 continues with operation 207 in which the photo resist layer and the ARC layer over the top surface of each mesa are removed. It is understood that the method 200 includes steps having features of a typical CMOS technology process flow and thus, are only described briefly herein. Further, it is understood that additional steps can be provided before, during, and after the method 200. Some of the steps described below can be replaced or eliminated for additional embodiments of the method 200.

FIGS. 3A and 4 through 9 are cross-sectional views of a structure 104 in a MEMS chip having a MEMS nanostructure at various stages of manufacture according to various embodiments of the method 200 of FIG. 2. Various figures have been simplified for a better understanding of the inventive concepts of the present disclosure.

Figure 3A:
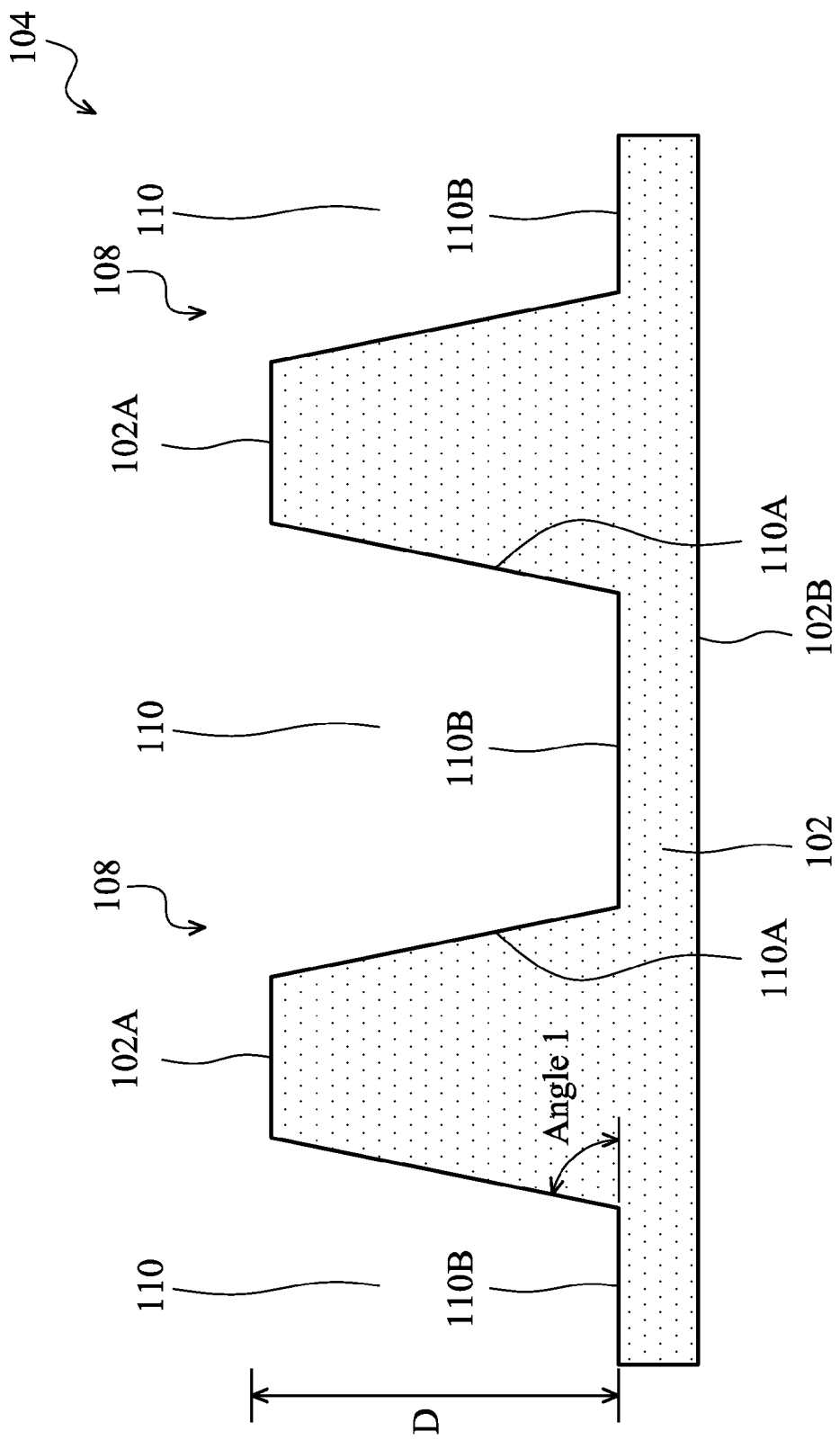
FIGS. 3A and 4 through 9 are cross-sectional views of a structure of the MEMS chip having a MEMS nanostructure at various stages of manufacture according to various embodiments of the method of FIG. 2.

Referring to FIG. 3A, which is an enlarged cross-sectional view of a portion of a structure 104 in a MEMS chip after performing operation 201. In FIG. 3A, a portion of a substrate 102 is recessed to form a plurality of mesas 108. The recessed portion of the substrate 102 forms a plurality of recesses 110 surrounding each mesa 108. The adjacent mesas 108 are separated by a recess 110. The recess operation 201 may be formed by using suitable photolithography process to provide a pattern on the substrate 102. Then, etching processes are performed to remove a portion of the substrate 102 to define the plurality of mesas 108. The etching processes may include wet etch, dry etch, plasma etch and/or other suitable processes.

Figure 3C:
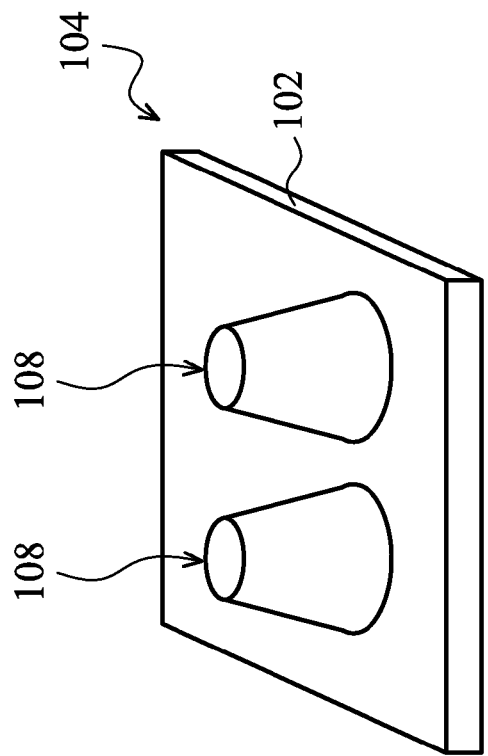
FIG. 3C is a perspective view of the single MEMS chip along line A-A' in FIG. 3B according to one or more embodiments of this disclosure.
Figure 3B:
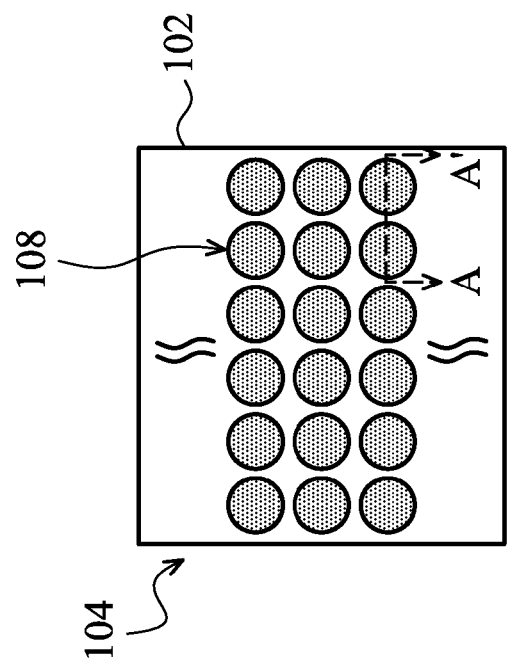
FIG. 3B is a top view of the structure of the single MEMS chip of FIG. 3A according to one or more embodiments of this disclosure.

In one embodiment, the mesas 108 are in an arrangement of an array as shown in FIG. 3B with a top view of the structure 104. FIG. 3C is a perspective view of the mesas 108 along line A-A' in FIG. 3B. FIG. 3A is the cross-sectional view of the mesas 108 along line A-A' in FIG. 3B. The substrate 102 has a top surface 102A and a bottom surface 102B. The recesses 110 extend from the top surface 102A into the substrate 102 with a depth D of about 2 μm to 10 μm, while not penetrating through the bottom surface 102B. The recess 110 has an interior surface 110A and a bottom surface 110B. The mesa 108 has a top surface and a sidewall surface adjacent to the top surface. The top surface of the mesa 108 is the same as the top surface 102A of the substrate 102. The sidewall surface of the mesa 108 is the same as the interior surface 110A of the recess 110. In one example, the mesa 108 has an interior angle, Angle 1, between a plane parallel to the bottom surface 110B and the interior surface 110A, in a range from about 60° to about 85°.

Figure 4:
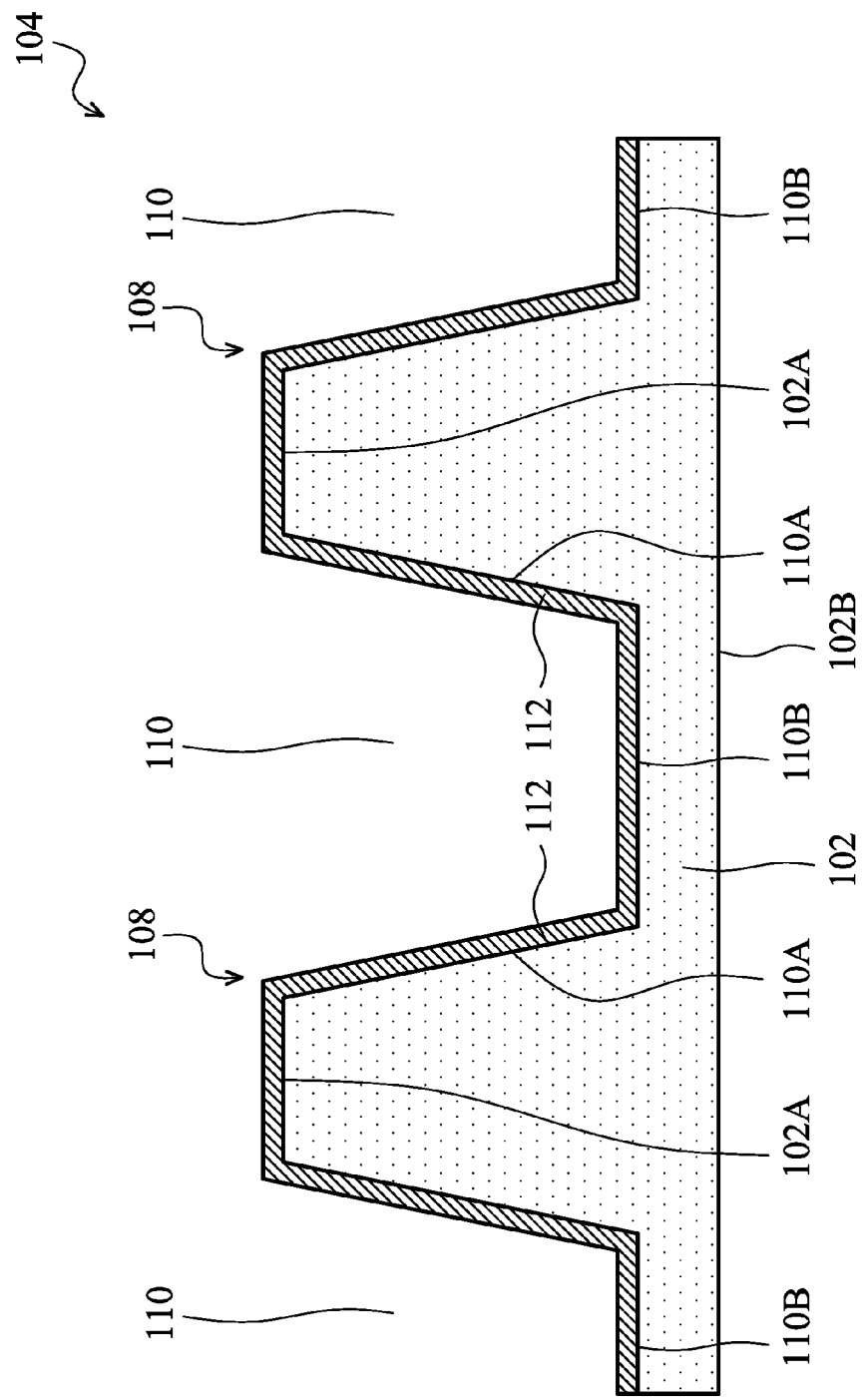
Figure 10:
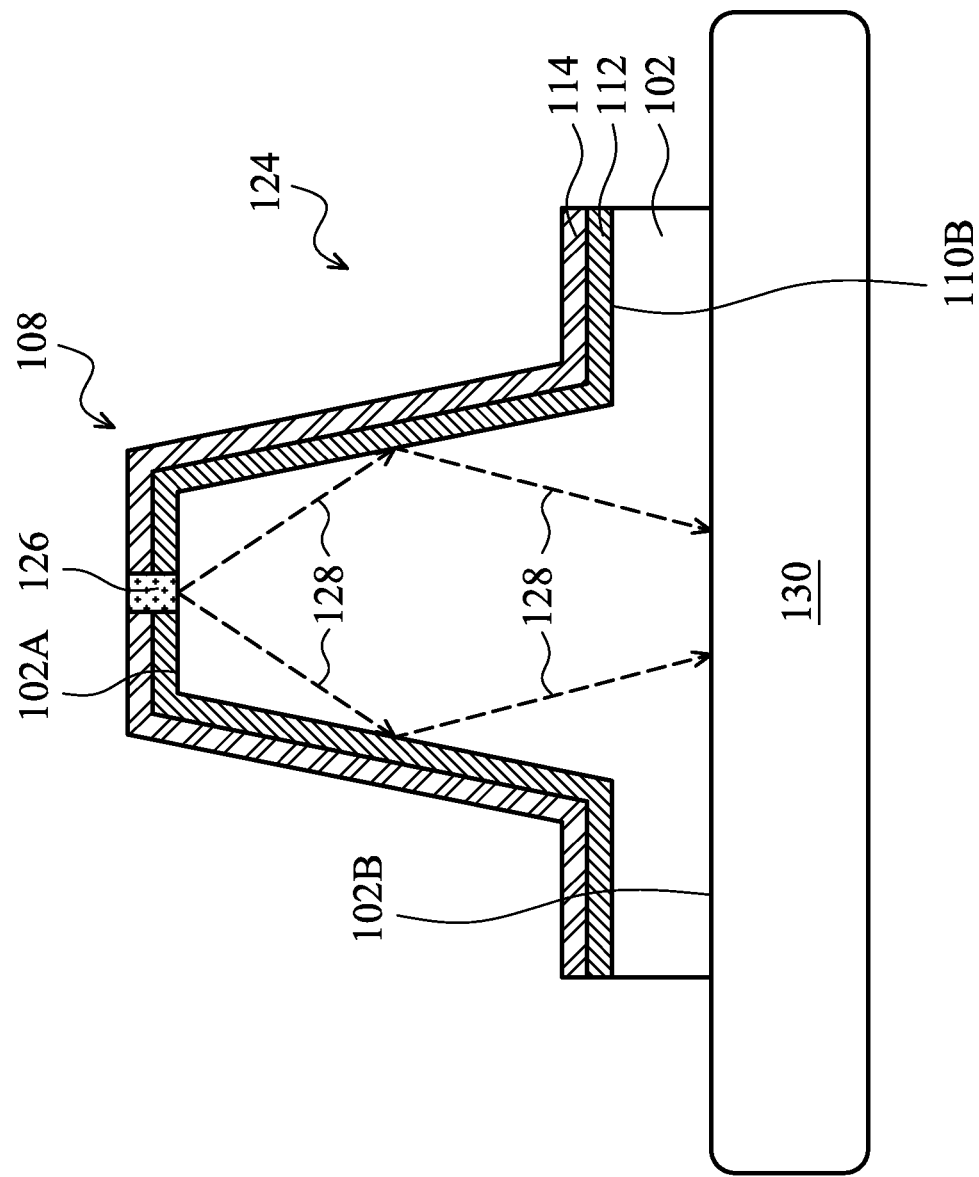
FIG. 10 illustrates an enlarged cross-sectional view of a MEMS nanostructure in an operation of detecting biomolecules according to one or more embodiments.

Referring back to FIG. 2, the method 200 continues with operation 202. FIG. 4 illustrates a cross-sectional view of the structure 104 for the manufacture stage after a light reflecting layer 112 is deposited over the substrate 102 to cover each mesa 108. The light reflecting layer 112 covers the top surface 102A, the interior surface 110A and the bottom surface 110B of each recess 110. In one example, the light reflecting layer 112 has a thickness in a range from about 1000 Å to about 5000 Å. The mesa 108 and the light reflecting layer 112 disposed on outside surfaces (e.g., top surface 102A and interior surface 110A) of the mesa 108 is configured as a micro-mirror in one example. The light reflecting layer 112 may enhance the reflectivity of the outside surfaces (102A and 110A) of the mesa 108. An operation of the micro-mirror will be explained further in the later section as shown in FIG. 10.

The light reflecting layer 112 is an opaque or reflective material. In some embodiments, the light reflecting layer 112 may be compatible (e.g., friendly) for bio-entity binding. In other embodiments, the light reflecting layer 112 includes a metallic material such as aluminum, copper, gold, silver, chromium, titanium or mixtures thereof. In the present example, the light reflecting layer 112 is an aluminum-copper layer (also referred to as aluminum-copper layer 112). The light reflecting layer 112 may be formed by a suitable process, such as physical vapor deposition (PVD), chemical vapor deposition (CVD) or atomic layer deposition (ALD). In other embodiments, the light reflecting layer 112 can also comprise a reflective organic polymer, such as a composite material comprising reflective particles dispersed in a polymeric material.

Figure 5:
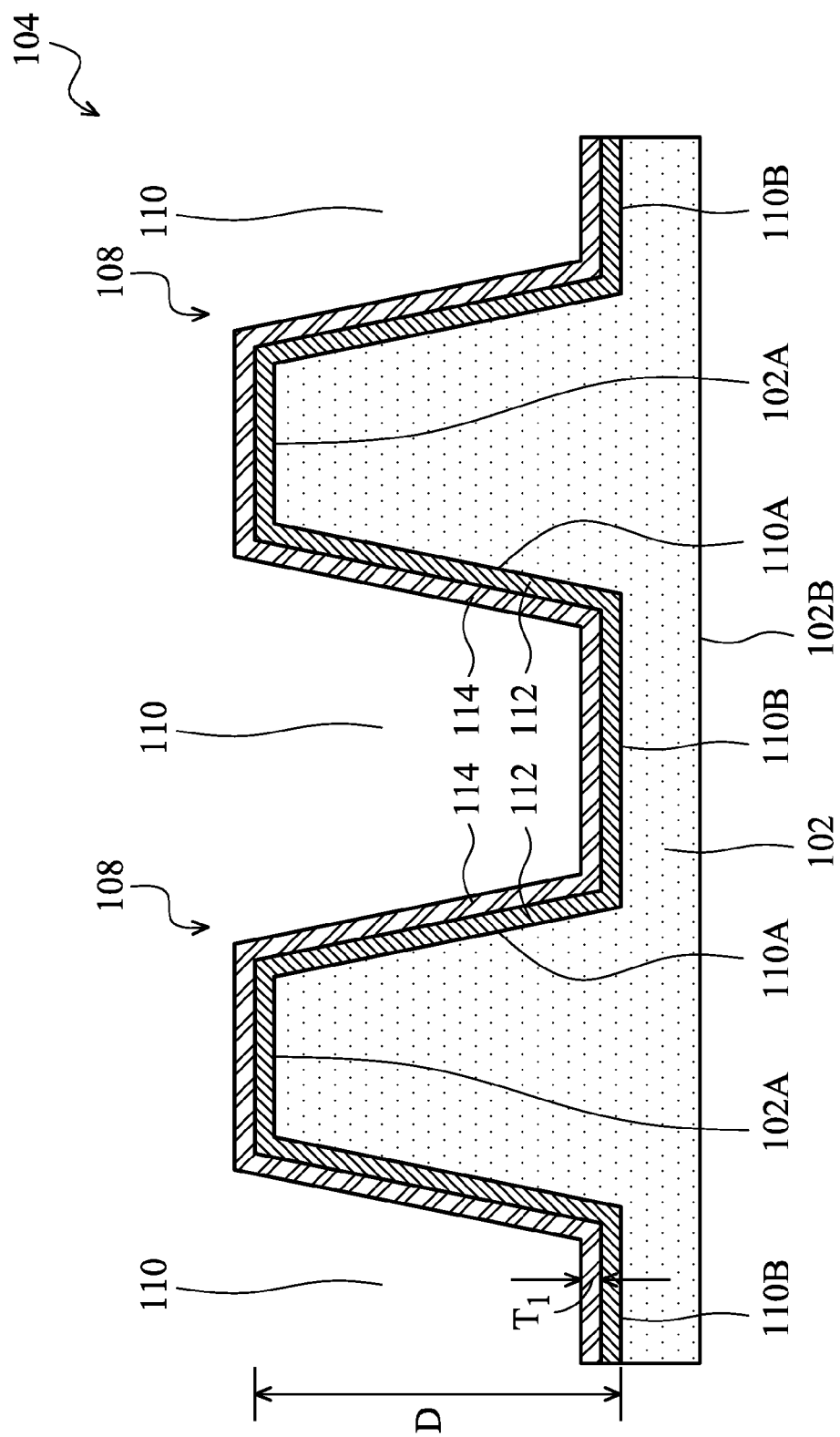

Referring back to FIG. 2, the method 200 continues with operation 203. FIG. 5 illustrates a cross-sectional view of the structure 104 for the manufacture stage after a protection layer 114 is formed over the light reflecting layer 112 over each mesa 108. In some embodiments, the protection layer 114 includes oxide layer, nitride layer or other suitable materials which prevent a metal complex from forming on the underlying light reflecting layer 112 in the following processes. In some examples, the protection layer 114 is a conformal liner along a top surface of the light reflecting layer 112. The protection layer 114 has a thickness $T_1$ less than the depth D of the recesses 110.

In the present example, the protection layer 114 is an aluminum oxide layer. The light reflecting layer 112 (e.g., an aluminum-copper layer) is treated in a plasma environment comprising oxygen to form the protection layer 114 (e.g., an aluminum oxide layer. The plasma environment comprises a carrier gas such as He, $N_2$, or Ar. The carrier gas helps to control the plasma density and treatment uniformity. In one embodiment, a flow rate of oxygen is in a range of about 5 standard cubic centimeters per minute (sccm) to about 500 sccm. A flow rate of $N_2$ is in a range of about 10% to about 90% of total gases of the chamber for the plasma environment. An operation power of the plasma environment is about 100 W to about 5000 W. An operation pressure of the plasma environment is about 5 mTorr to about 500 mTorr. A thickness $T_1$ of the protection layer 114 is in a range from about 10 Å to about 300 Å. In other examples, the protection layer 114 may be formed by plasma enhanced chemical vapor deposition (PECVD), high aspect ratio process (HARP) or atomic layer deposition (ALD).

Figure 6:
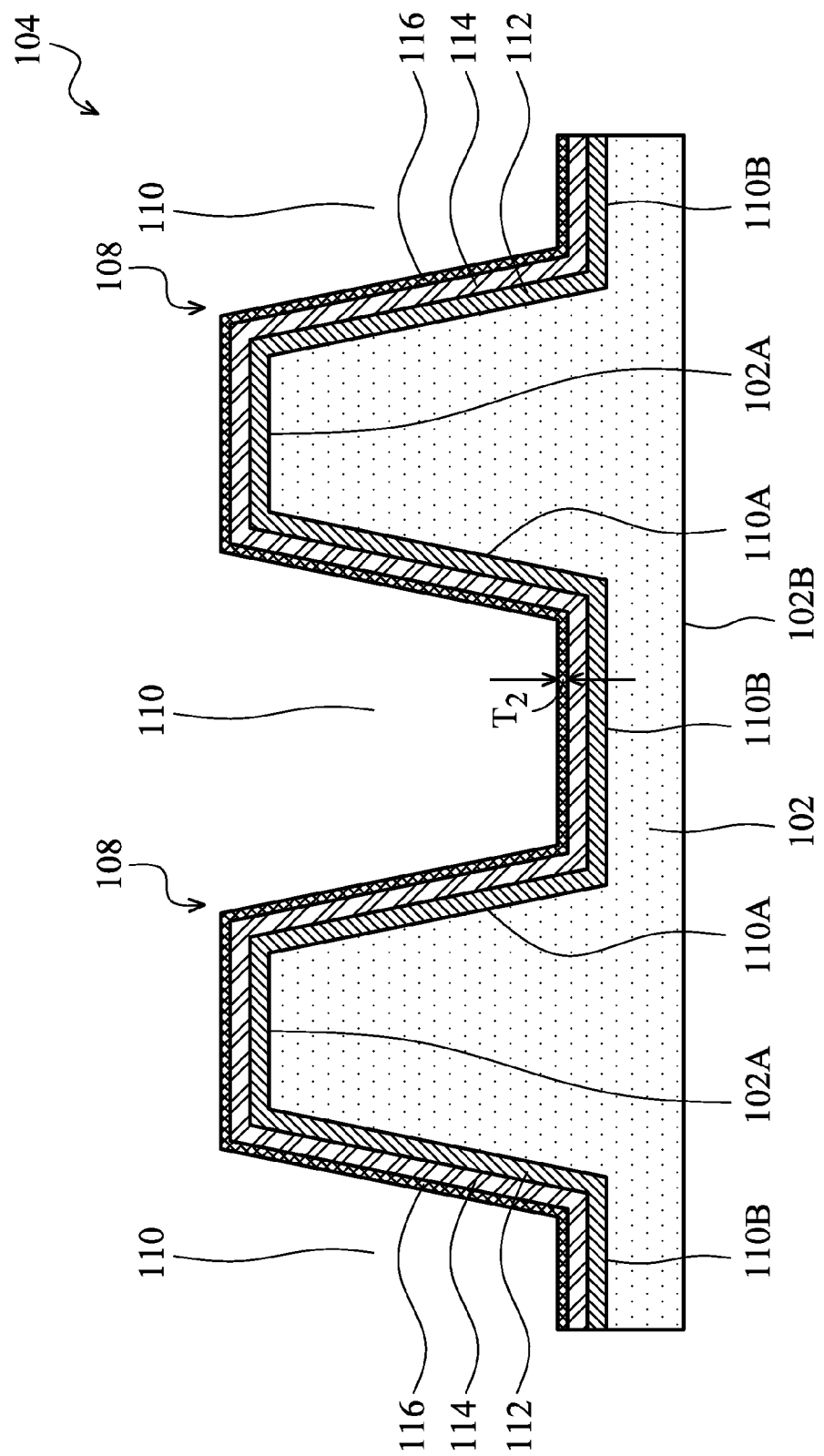

Referring back to FIG. 2, the method 200 continues with operation 204. FIG. 6 illustrates a cross-sectional view of the structure 104 for the manufacture stage after an anti-reflective coating (ARC) layer 116 is formed over the protection layer 114. In some embodiments, the ARC layer 116 includes titanium nitride, silicon oxynitride or other suitable materials which reduce unintended light reflection in the following photo resist exposure process. In some examples, the ARC layer 116 is a conformal liner along a top surface of the protection layer 114. In the present example, the ARC layer 116 is a titanium nitride layer having a thickness $T_2$ in a range from about 50 Å to about 300 Å. The ARC layer 116 may be formed by plasma enhanced chemical vapor deposition (PECVD), high aspect ratio process (HARP) or atomic layer deposition (ALD).

Figure 7A:
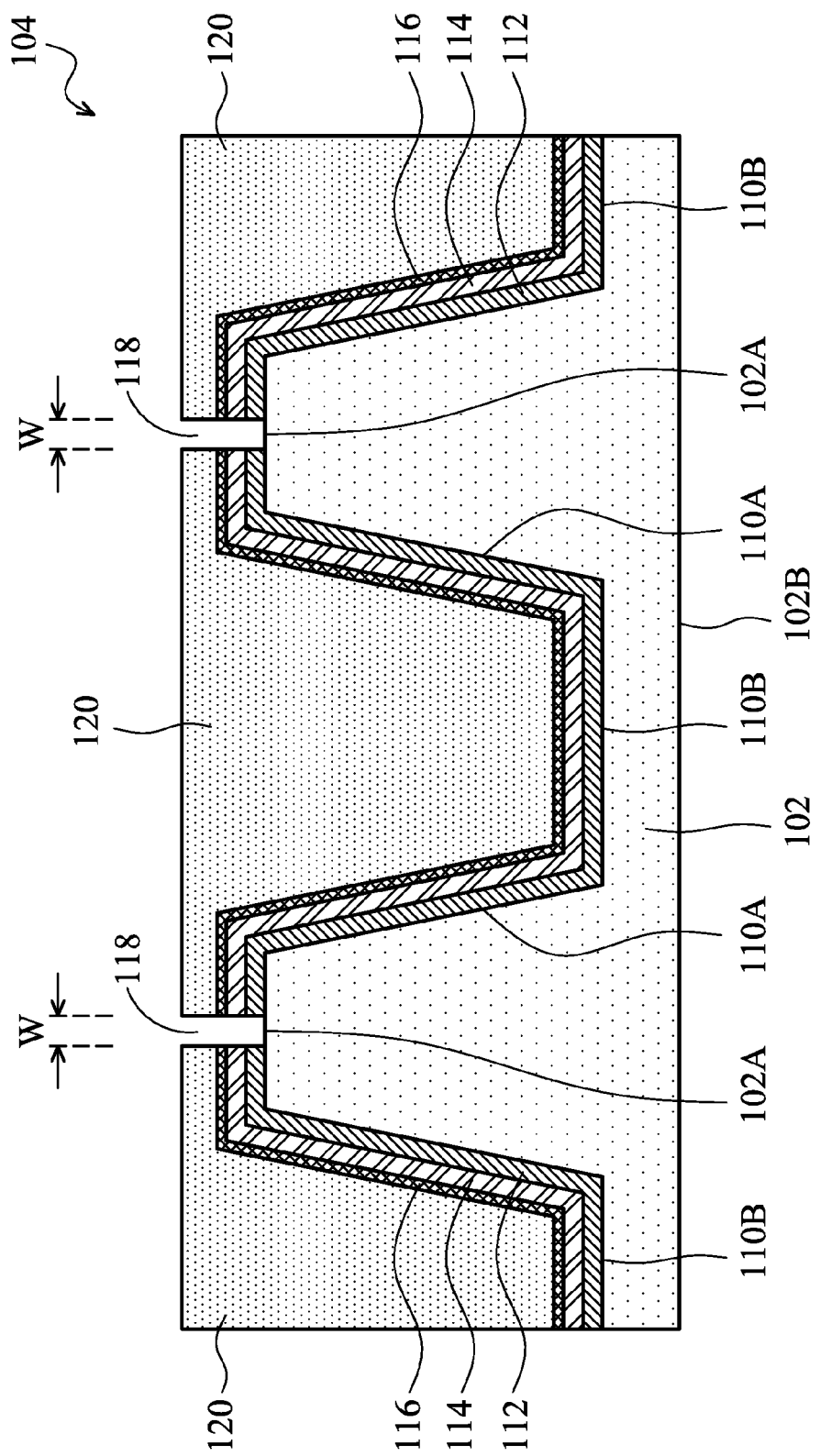

Referring back to FIG. 2, the method 200 continues with operations 205 and 206. FIG. 7A illustrates a cross-sectional view of the structure 104 for the manufacture stage after an opening 118 is formed in a photo resist layer 120 over the ARC layer 116 for each mesa 108. The photo resist layer 120 is formed over the structure 104 shown in FIG. 6 to a level above top surfaces of the mesas 108 and the ARC layer 116 by lithography patterning processes. The lithography patterning processes include photoresist coating (e.g., spin-on coating), soft baking, mask aligning, exposure, post-exposure baking, developing the photoresist, rinsing, drying (e.g., hard baking) or combinations thereof. The openings 118 are formed over the mesas 108 after the lithography patterning processes. In at least one example, the opening 118 has a width W in a range from about 110 nm to about 170 nm. Advantageously, the ARC layer 116 beneath the photo resist layer 120 reduces standing wave effects in the photo resist layer 120. The critical dimension (CD) of the width W for the opening 118 could be accurately controlled.

Still referring to FIG. 7A, the patterned photo resist layer 120 is then subjected to etching process to remove a portion of the ARC layer 116, the protection layer 114 and the light reflecting layer 112 through the opening 118. A portion of the top surface 102A of each mesa 108 is exposed and the opening 118 is also defined within the ARC layer 116, the protection layer 114 and the light reflecting layer 112. In some embodiments, the opening 118 is capable of containing an observed analyte. The analyte may include an enzyme, an antibody, a ligand, a peptide or an oligonucleotide. In at least one example, the width W of the opening 118 is capable of containing only one molecule of the analyte. The width W contains part of a DNA (deoxyribonucleic acid) strand and polymerase within the opening 118.

Figure 7B:
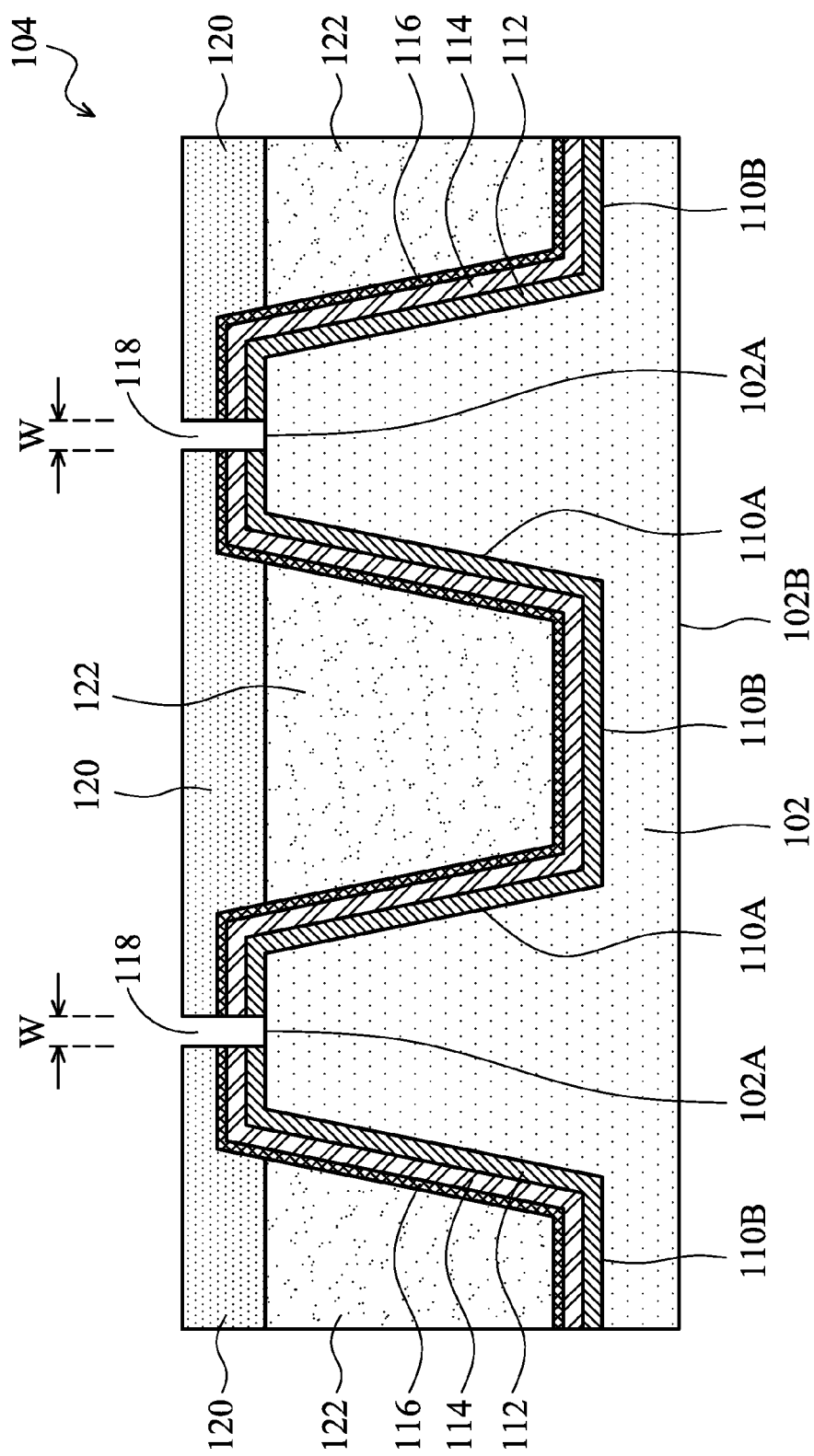

FIG. 7B illustrates a cross-sectional view of the structure 104 for another embodiment in the manufacture stage for forming the opening 118 for each mesa 108. Before operations 205 and 206, a filling material 122 is filled in the recesses 110 surrounding each mesa 108 and planarized to a level substantially planar to the top surface 102A of the mesas 108. A portion of the ARC layer 116 over the top surface 102A is exposed. Then, the photo resist layer 120 is formed over the exposed ARC layer 116 and the filling material 122. In some examples, the filling material 122 includes silicon oxide, dielectric material, polycrystalline silicon, amorphous silicon or combinations thereof. The filling material 122 is formed by low temperature chemical vapor deposition (LTCVD) at an operation temperature less than 300° C. to prevent damaging the substrate 102 for electrical or optical signals detection. Advantageously, the planarized filling material 122 and the ARC layer 116 over the surface 102A form a smooth surface. The smooth surface enhances the capability to achieve a better resolution of the following lithography process on the smooth surface.

Figure 8:
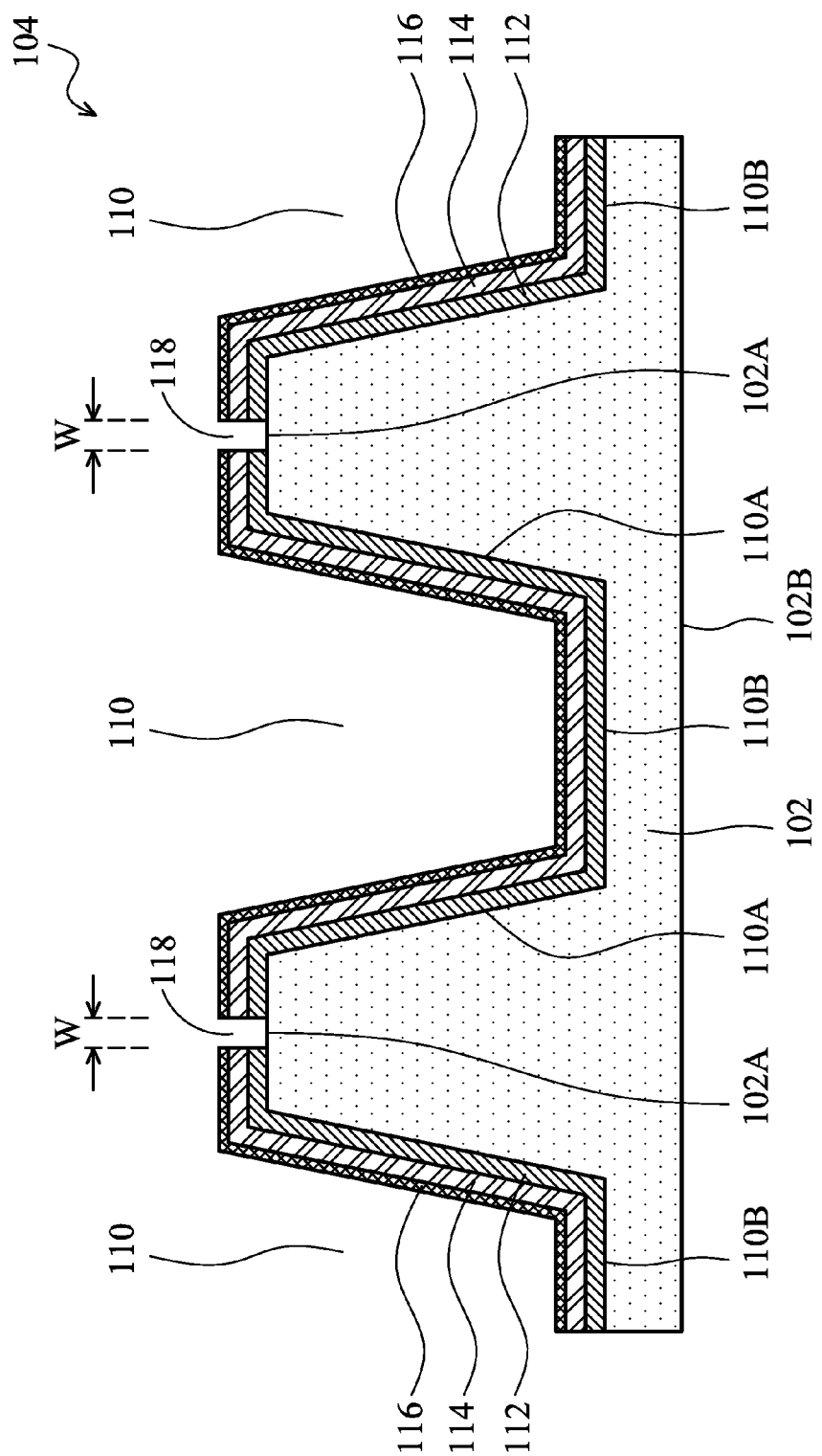
Figure 9:
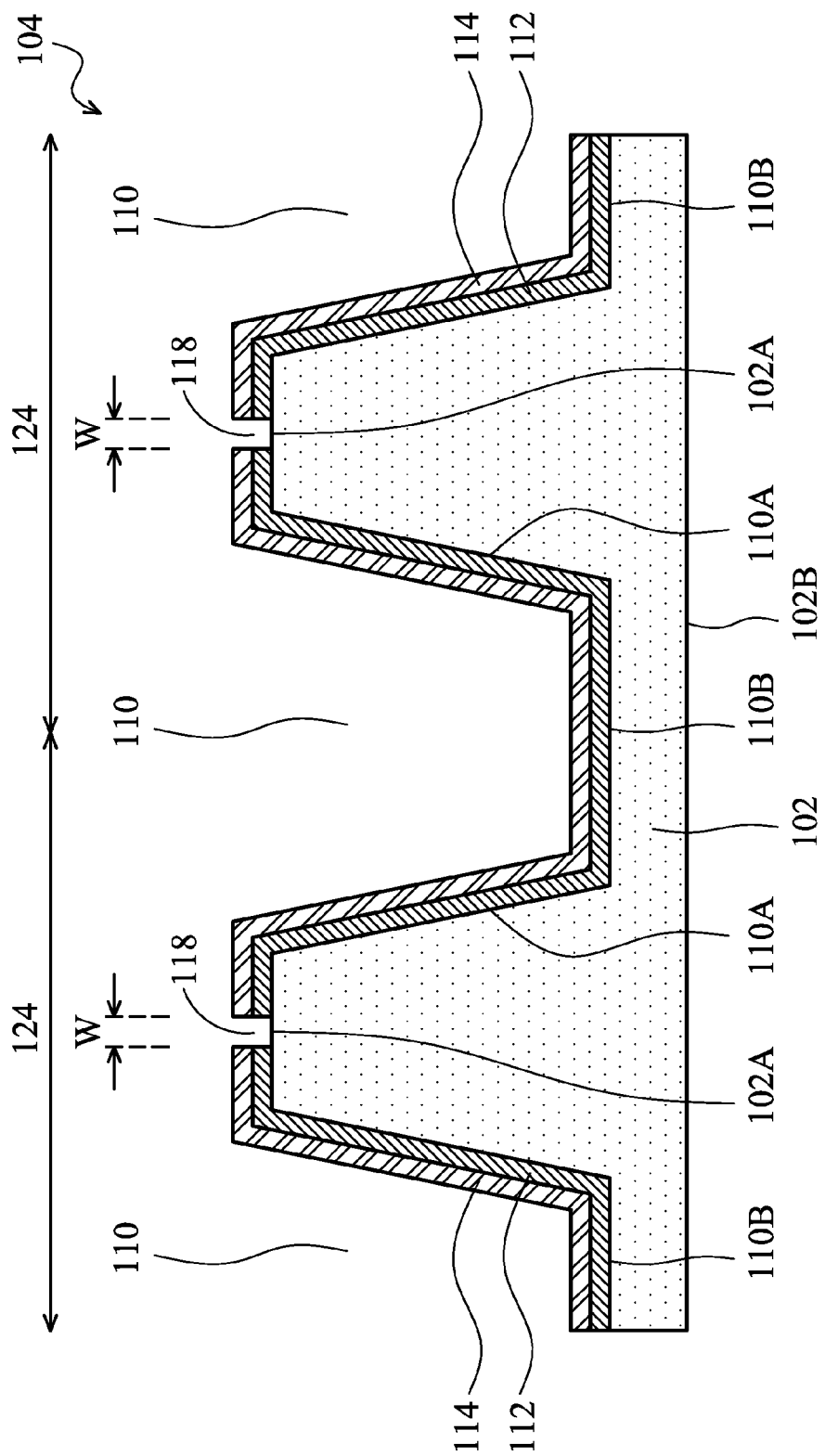

Referring back to FIG. 2, the method 200 continues with operation 207 which is illustrated in FIGS. 8 and 9. In FIG. 8, the photo resist layer 120 is removed from the structure 104. In some examples, the photo resist layer 120 is ashed in a plasma environment comprising oxygen. In other examples, the photo resist layer 120 is stripped in wet chemical solutions.

In FIG. 9, the ARC layer 116 is removed from the structure 104. In some examples, wet chemical solutions are used to selectively remove the ARC layer 116 and without substantially etch the underlying protection layer 114. In the present example, the ARC layer 116 is a titanium nitride layer. The titanium nitride layer is removed in a wet solution comprising $H_2O_2$. In one embodiment, a flow rate of $H_2O_2$ is in a range of about 10 standard cubic centimeters per minute (sccm) to about 500 sccm. An operation temperature is in a range of about 40 to about 70° C. In one example shown in FIG. 7A, the entire ARC layer 116 over each mesa 108 is removed and the protection layer 114 is exposed. In another example shown in FIG. 7B, the exposed ARC layer 116 over the filling material 122 is removed. Other portion of the ARC layer 116 is embedded in the filling material 122. Advantageously, the protection layer 114 protects the underlying layers during the ARC layer 116 removal and prevents damaging the light reflecting layer 112 and the substrate 102 for electrical or optical signals detection. Additionally, the protection layer 114 is formed between the ARC layer 116 and the light reflecting layer 112. The protection layer 114 prevents any residual of the ARC layer 116 from forming a metal complex with the underlying light reflecting layer 112. In the operation of detecting biomolecules, the observed analyte is free of interfering by the metal complex.

After the operation 207, a MEMS nanostructure 124 having a micro-mirror is formed in the structure 104 of MEMS chip.

In some embodiments, further process steps are optionally included after the operation 207. In some embodiments, a mechanically sawing or a laser sawing is performed along the scribe lines 106 of the wafer 100 and the substrate 102 are sawed into individual MEMS chips 103.

FIG. 10 illustrates an enlarged cross-sectional view of a MEMS nanostructure 124 in an operation of detecting biomolecules. The MEMS nanostructure 124 includes a mesa 108 integrally connected a portion of a substrate 102. The mesa 108 has the top surface corresponding to the top surface 102A of the substrate 102 and the sidewall surface adjacent to the top surface and corresponding to sidewall surface 110A of recess 110. A light reflecting layer 112 is disposed over the top surface 102A and the sidewall surface 110A. The mesa 108 and the light reflecting layer 112 disposed on the outside surfaces (102A and 110A) of the mesa 108 is configured as a micro-mirror. A protection layer 114 is disposed over the light reflecting layer 112. An opening is disposed in the protection layer 114 and the light reflecting layer 112 to partially expose the portion of the top surface 102A of the substrate 102. During the detecting operation as a biological sensor, an analyte 126 is disposed in the opening of the MEMS nanostructure 124. The analyte 126 may include an enzyme, an antibody, a ligand, a peptide or an oligonucleotide. A source of excitation radiation (not shown) generates radiation incident on the analyte 126. The analyte 126 may emit a light output 128 to the underneath micro-mirror. The micro-mirror reflects the light output 128 and conveys the light output 128 to a detector 130 below the bottom surface 102B of substrate 102. The detector 130 collects the light output 128 and stores the light output 128 in a storage apparatus for analysis. The light reflecting layer 112 may enhance the reflectivity of the outside surfaces (102A and 110A) of the mesa 108.

One aspect of the disclosure describes a method of forming a plurality of MEMS nanostructures. A portion of a substrate is recessed to form a plurality of mesas in the substrate. Each of the plurality of mesas has a top surface and a sidewall surface adjacent to the top surface. A light reflecting layer is deposited over the substrate thereby covering the top surface and the sidewall surface of each mesa. A protection layer is formed over the light reflecting layer. An ARC layer is formed over the protection layer. An opening in a photo resist layer is formed over the ARC layer over each mesa. A portion of the ARC layer, the protection layer and the light reflecting layer are removed through the opening to expose the top surface of each mesa. The photo resist layer and the ARC layer over the top surface of each mesa are removed.

A further aspect of the disclosure describes a method of forming a plurality of MEMS nanostructures. A portion of a substrate is recessed to form a plurality of mesas in the substrate. Each of the plurality of mesas has a top surface and a sidewall surface adjacent to the top surface. A light reflecting layer is deposited over the substrate thereby covering the top surface and the sidewall surface of each mesa. A protection layer is conformally formed along the light reflecting layer. An ARC layer is formed over the protection layer. An opening in a photo resist layer is formed over the ARC layer over each mesa. A portion of the ARC layer, the protection layer and the light reflecting layer are removed through the opening to expose the top surface of each mesa. The photo resist layer and the ARC layer are removed without substantially removing the protection layer.

Another aspect of the disclosure describes a method of forming a plurality of MEMS nanostructures. A portion of a substrate is recessed to form a plurality of mesas in the substrate. Each of the plurality of mesas has a top surface and a sidewall surface adjacent to the top surface. A light reflecting layer is deposited over the substrate thereby covering the top surface and the sidewall surface of each mesa. A protection layer is formed over the light reflecting layer. An ARC layer is formed over the protection layer. A filling material is formed surrounding each mesa to expose a portion of the ARC layer. An opening in a photo resist layer is formed over the exposed ARC layer over each mesa. A portion of the exposed ARC layer, the protection layer and the light reflecting layer are removed through the opening to expose the top surface of each mesa. The photo resist layer and the exposed portion of the ARC layer are removed.

An aspect of this description relates to a method of forming a semiconductor device. The method comprises depositing a light reflecting layer over a substrate. The method also comprises forming a protection layer over the light reflecting layer. The method further comprises forming an anti-reflective coating (ARC) layer over the protection layer. The method additionally comprises forming an opening in the ARC layer, the protection layer and the light reflecting layer exposing the substrate. The method also comprises removing the ARC layer in a wet solution comprising H2O2, the ARC layer being exposed to the H2O2 at a flow rate greater than about 10 standard cubic centimeters per minute (sccm).

Another aspect of this description relates to a method of forming a semiconductor device. The method comprises depositing a light reflecting layer over a substrate. The method also comprises forming a protection layer over the light reflecting layer. The method further comprises forming an anti-reflective coating (ARC) over the protection layer. The method additionally comprises forming an opening in the ARC layer, the protection layer and the light reflecting layer exposing the substrate. The method also comprises removing the ARC layer without substantially removing the protection layer using a wet solution comprising H2O2. The ARC layer is exposed to the H2O2 at a flow rate greater than about 10 standard cubic centimeters per minute (sccm).

A further aspect of this description relates to a method of forming a semiconductor device. The method comprises depositing a light reflecting layer over a substrate having at least one mesa structure. The at least one mesa structure has a top surface and a sidewall adjacent the top surface. The light reflecting layer is deposited so as to cover the top surface of the at least one mesa structure. The method also comprises forming a protection layer over the light reflecting layer. The method further comprises forming an anti-reflective coating (ARC) layer over the protection layer. The method additionally comprises forming a filling material surrounding the at least one mesa leaving a portion of the ARC layer exposed. The method also comprises forming an opening in the exposed portion of the ARC layer, the protection layer and the light reflecting layer exposing the top surface of the at least one mesa. The method further comprises removing the exposed portion of the ARC layer in a wet solution comprising H2O2, the ARC layer being exposed to the H2O2 at a flow rate greater than about 10 standard cubic centimeters per minute (sccm).

Although the embodiments and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed:

1. A method of forming a semiconductor device, the method comprising:
depositing a light reflecting layer over a substrate having at least two protruded portions separated by a recess region, the recess region having a depth extending from a bottom of the recess to a top of at least one of the protruded portions;
treating the light reflecting layer in a plasma environment comprising oxygen until a protection layer comprising aluminum oxide and having a thickness in the recess region less than the depth of the recess region is formed over the light reflecting layer;
forming an anti-reflective coating (ARC) layer comprising titanium nitride directly on the protection layer;
forming an opening in the ARC layer, the protection layer and the light reflecting layer exposing the substrate; and
removing the ARC layer in a wet solution comprising $H_2O_2$, the ARC layer being exposed to the $H_2O_2$ at a flow rate greater than about 10 standard cubic centimeters per minute (sccm).

2. The method of claim 1, wherein the light reflecting layer comprises aluminum, copper, gold, silver, chromium, titanium or mixtures thereof.

3. The method of claim 1, wherein the opening has a width capable of containing only one molecule of an analyte.

4. The method of claim 1, wherein the opening has a width in a range from about 110 nanometers (nm) to about 170 nm.

5. The method of claim 1, wherein the thickness of the protection layer in the recess region is in a range from about 10 Å to about 300 Å.

6. The method of claim 1, wherein removing the ARC layer in the wet solution comprising $H_2O_2$ leaves a quantity of the protection layer capable of preventing formation of a metal complex resulting from residual ARC layer.

7. The method of claim 1, wherein the ARC layer is removed at a process temperature of about 40° C. to about 70° C.

8. A method of forming a semiconductor device, the method comprising:
- depositing a light reflecting layer over a substrate having at least two protruded portions separated by a recess region, the recess region having a depth extending from a bottom of the recess to a top of at least one of the protruded portions;
- treating the light reflecting layer in a plasma environment comprising oxygen until a protection layer comprising aluminum oxide and having a thickness in the recess region less than the depth of the recess region and within a predetermined range is formed over the light reflecting layer;
- forming an anti-reflective coating (ARC) comprising titanium nitride over the protection layer;
- forming an opening in the ARC layer, the protection layer and the light reflecting layer exposing the substrate, wherein forming the opening comprises depositing a photoresist layer over the ARC, and a bottom surface of the photoresist layer is below a top-most surface of the light reflecting layer; and
- removing the ARC layer without substantially removing the protection layer using a wet solution comprising $H_2O_2$, the ARC layer being exposed to the $H_2O_2$ at a flow rate greater than about 10 standard cubic centimeters per minute (sccm).

9. The method of claim 8, the light reflecting layer comprises aluminum, copper, gold, silver, chromium, titanium or mixtures thereof.

10. The method of claim 8, wherein the opening has a width capable of containing only one molecule of an analyte.

11. The method of claim 8, wherein the opening has a width in a range from about 110 nm to about 170 nm.

12. The method of claim 8, wherein the ARC layer is removed at a process temperature of about 40° C. to about 70° C.

13. A method of forming a semiconductor device, the method comprising:
- depositing a light reflecting layer over a substrate having at least one mesa structure, the at least one mesa structure having a top surface and a sidewall adjacent the top surface, the light reflecting layer being deposited so as to cover the top surface of the at least one mesa structure;
- treating the light reflecting layer in a plasma environment comprising oxygen to form a protection layer comprising aluminum oxide over the light reflecting layer;
- forming an anti-reflective coating (ARC) layer comprising titanium nitride over the protection layer;
- forming a filling material surrounding the at least one mesa leaving a portion of the ARC layer exposed, wherein a top surface of the filling material is below a top-most surface of the ARC;
- forming an opening in the exposed portion of the ARC layer, the protection layer and the light reflecting layer exposing the top surface of the at least one mesa; and
- removing the exposed portion of the ARC layer in a wet solution comprising $H_2O_2$, the ARC layer being exposed to the $H_2O_2$ at a flow rate greater than about 10 standard cubic centimeters per minute (sccm),
- wherein the sidewall has a length, and the light reflecting layer is treated in the plasma environment until the protection layer has a thickness in a region adjacent to the sidewall of the at least one mesa structure that is less than the length of the sidewall of the at least one mesa structure.

14. The method of claim 13, wherein the light reflecting layer comprises aluminum, copper, gold, silver, chromium, titanium or mixtures thereof.

15. The method of claim 13, the filling material comprises one or more of silicon oxide, dielectric material, polycrystalline silicon, or amorphous silicon.

16. The method of claim 13, wherein the opening has a width capable of containing only one molecule of an analyte.

17. The method of claim 13, wherein the opening has a width in a range from about 110 nm to about 170 nm.

18. The method of claim 13, wherein the ARC layer is removed at a process temperature of about 40° C. to about 70° C.

19. The method of claim 13, wherein the thickness of the protection layer in the recess region is in a range from about 10 Å to about 300 Å.

20. The method of claim 13, wherein removing the ARC layer in the wet solution comprising $H_2O_2$ leaves a quantity of the protection layer capable of preventing formation of a metal complex resulting from residual ARC layer.

* * * * *